United States Patent
Kim et al.

(10) Patent No.: US 9,366,757 B2
(45) Date of Patent: Jun. 14, 2016

(54) ARRANGING A THREE-DIMENSIONAL ULTRASOUND IMAGE IN AN ULTRASOUND SYSTEM

(75) Inventors: Chul An Kim, Seoul (KR); Sung Yoon Kim, Seoul (KR); Sung Mo Lee, Seoul (KR)

(73) Assignee: SAMSUNG MEDISON CO., LTD., Hongcheon-Gun, Gangwon-Do (KR)

( * ) Notice: Subject to any disclaimer, the term of this patent is extended or adjusted under 35 U.S.C. 154(b) by 314 days.

(21) Appl. No.: 12/729,047

(22) Filed: Mar. 22, 2010

(65) Prior Publication Data

US 2010/0274132 A1 Oct. 28, 2010

(30) Foreign Application Priority Data

Apr. 27, 2009 (KR) .................. 10-2009-0036300

(51) Int. Cl.
*A61B 8/00* (2006.01)
*G01S 15/89* (2006.01)
(Continued)

(52) U.S. Cl.
CPC ............. *G01S 15/8993* (2013.01); *A61B 8/483* (2013.01); *G06T 7/0046* (2013.01); *G06T 15/08* (2013.01);
(Continued)

(58) Field of Classification Search
CPC ........... A61B 2019/5276; A61B 8/483; A61B 8/461; A61B 8/463; A61B 2019/507; A61B 6/463; A61B 8/523; A61B 2019/5295
USPC ................ 600/407, 467–472; 345/1.1–9, 345/156–184, 204–210, 418–472.3, 345/501–522, 690–699; 382/128, 130–134, 382/173, 174, 254–308, 318–321
See application file for complete search history.

(56) References Cited

U.S. PATENT DOCUMENTS 4,630,203 A * 12/1986 Szirtes .......................... 382/132
5,371,778 A * 12/1994 Yanof et al. ...................... 378/4
(Continued)

FOREIGN PATENT DOCUMENTS

EP 1717758 A2 11/2006
JP 63-168152 7/1988
(Continued)

OTHER PUBLICATIONS

Extended European Search Report for EP 10156169.4-2220, 9 pages, mailed Aug. 19, 2010.
(Continued)

*Primary Examiner* — Mark Remaly
(74) *Attorney, Agent, or Firm* — McDermott Will & Emery LLP (57) ABSTRACT

Embodiments for arranging a 3D (three-dimensional) ultrasound image are disclosed. In one embodiment, by way of non-limiting example, an ultrasound system comprises: a storage unit for storing a plurality of reference position information each corresponding to a plurality of target objects; a user input unit configured to receive input information for selecting a target object; an ultrasound data acquisition unit configured to transmit and receive ultrasound signals to and from the target object to thereby output ultrasound data; and a processing unit in communication with the storage unit, the user input unit and the ultrasound data acquisition unit, the processing unit being configured to form a 3D ultrasound image based on the ultrasound data and perform position arrangement of the 3D ultrasound image based on reference position information corresponding to the input information.

17 Claims, 6 Drawing Sheets

(51) Int. Cl.
  *A61B 8/08*    (2006.01)
  *G06T 7/00*    (2006.01)
  *G06T 19/00*   (2011.01)
  *G06T 15/08*   (2011.01)

(52) U.S. Cl.
  CPC ....... *G06T 19/00* (2013.01); *G06T 2207/10136* (2013.01); *G06T 2207/30004* (2013.01); *G06T 2219/008* (2013.01)

(56) References Cited

U.S. PATENT DOCUMENTS

| | | | |
|---|---|---|---|
| 6,988,991 | B2 | 1/2006 | Kim et al. |
| 7,174,033 | B2 | 2/2007 | Yukhin et al. |
| 2004/0213445 | A1 | 10/2004 | Lee et al. |
| 2005/0096538 | A1* | 5/2005 | Chomas et al. ............ 600/437 |
| 2005/0195190 | A1* | 9/2005 | Williams et al. ........... 345/424 |
| 2006/0034513 | A1 | 2/2006 | Cai et al. |
| 2006/0067567 | A1 | 3/2006 | Hashimoto |
| 2006/0241445 | A1 | 10/2006 | Altmann et al. |
| 2007/0230758 | A1 | 10/2007 | Fan et al. |
| 2008/0186378 | A1 | 8/2008 | Shen et al. |

FOREIGN PATENT DOCUMENTS

| | | |
|---|---|---|
| JP | 6-254097 | 9/1994 |
| JP | 2003-325519 | 11/2003 |
| JP | 2006-305358 A | 11/2006 |
| JP | 2007-244575 A | 9/2007 |
| JP | 2008-188193 A | 8/2008 |
| JP | 2008-259764 | 10/2008 |
| KR | 10-2001-0026857 A | 4/2001 |

OTHER PUBLICATIONS

Korean Office Action issued in Korean Patent Application No. 10-2009-0036300, mailed Apr. 28, 2011.
Japanese Non-Final Rejection issued in Japanese Application No. 2010-064662 dated Jan. 7, 2014. (w/Partial English translation).
Notice of Allowance issued in Japanese Application No. 2010-064662 dated May 20, 2014, w/English translation.

* cited by examiner

| | X1 | X2 | X3 | X4 | X5 | X6 | X7 | |
|---|---|---|---|---|---|---|---|---|
| Z7 | $P_{X1,Z7}$ | $P_{X2,Z7}$ | $P_{X3,Z7}$ | $P_{X4,Z7}$ | $P_{X5,Z7}$ | $P_{X6,Z7}$ | $P_{X7,Z7}$ | |
| Z6 | $P_{X1,Z6}$ | $P_{X2,Z6}$ | $P_{X3,Z6}$ | $P_{X4,Z6}$ | $P_{X5,Z6}$ | $P_{X6,Z6}$ | $P_{X7,Z6}$ | |
| Z5 | $P_{X1,Z5}$ | $P_{X2,Z5}$ | $P_{X3,Z5}$ | $P_{X4,Z5}$ | $P_{X5,Z5}$ | $P_{X6,Z5}$ | $P_{X7,Z5}$ | |
| Z4 | $P_{X1,Z4}$ | $P_{X2,Z4}$ | $P_{X3,Z4}$ | $P_{X4,Z4}$ | $P_{X5,Z4}$ | $P_{X6,Z4}$ | $P_{X7,Z4}$ | |
| Z3 | $P_{X1,Z3}$ | $P_{X2,Z3}$ | $P_{X3,Z3}$ | $P_{X4,Z3}$ | $P_{X5,Z3}$ | $P_{X6,Z3}$ | $P_{X7,Z3}$ | |
| Z2 | $P_{X1,Z2}$ | $P_{X2,Z2}$ | $P_{X3,Z2}$ | $P_{X4,Z2}$ | $P_{X5,Z2}$ | $P_{X6,Z2}$ | $P_{X7,Z2}$ | |
| Z1 | $P_{X1,Z1}$ | $P_{X2,Z1}$ | $P_{X3,Z1}$ | $P_{X4,Z1}$ | $P_{X5,Z1}$ | $P_{X6,Z1}$ | $P_{X7,Z1}$ | |

330

ARRANGING A THREE-DIMENSIONAL ULTRASOUND IMAGE IN AN ULTRASOUND SYSTEM

CROSS-REFERENCE TO RELATED APPLICATIONS

The present application claims priority from Korean Patent Application No. 10-2009-0036300 filed on Apr. 27, 2009, the entire subject matter of which is incorporated herein by reference.

TECHNICAL FIELD

The present disclosure generally relates to ultrasound systems, and more particularly to arranging a 3D (three-dimensional) ultrasound image in an ultrasound system.

BACKGROUND

An ultrasound system has become an important and popular diagnostic tool since it has a wide range of applications. Specifically, due to its non-invasive and non-destructive nature, the ultrasound system has been extensively used in the medical profession. Modern high-performance ultrasound systems and techniques are commonly used to produce 2D (two-dimensional) or 3D (three-dimensional) ultrasound images of internal features of a target object (e.g., human organs).

The ultrasound system may provide the three-dimensional ultrasound image including clinical information such as spatial information and anatomical figures of the target object, which cannot be provided by the two-dimensional ultrasound image. The ultrasound system may transmit ultrasound signals into the target object, receive ultrasound echo signals reflected from the target objects and form volume data based on the ultrasound echo signals. The ultrasound system may further form the three-dimensional ultrasound image including the clinical information by rendering the volume data.

Generally, a position of the target object in the 3D ultrasound image is changed according to a position of an ultrasound probe, which transmits and receives ultrasound signals to and from the target object. Thus, there is a problem in that a user has to move or rotate the 3D ultrasound image in order to arrange the 3D ultrasound image.

SUMMARY

Embodiments for providing a plurality of slice images in an ultrasound system are disclosed herein. In one embodiment, by way of non-limiting example, an ultrasound system comprises: a storage unit for storing a plurality of reference position information each corresponding to a plurality of target objects; a user input unit configured to receive input information for selecting a target object; an ultrasound data acquisition unit configured to transmit and receive ultrasound signals to and from the target object to thereby output ultrasound data; and a processing unit in communication with the storage unit, the user input unit and the ultrasound data acquisition unit, the processing unit being configured to form a 3D ultrasound image based on the ultrasound data and perform position arrangement of the 3D ultrasound image based on reference position information corresponding to the input information.

In another embodiment, there is provided a method of arranging a 3D ultrasound image, comprising: a) receiving input information for selecting a target object; b) transmitting and receiving ultrasound signals to and from the target object to thereby output ultrasound data; c) forming a 3D ultrasound image based on the ultrasound data; and d) performing a position arrangement of the 3D ultrasound image based on reference position information corresponding to the input information, wherein the reference position information is stored in a storage unit corresponding to a plurality of target objects.

In yet another embodiment, there is provided a computer readable medium comprising computer executable instructions configured to perform the following acts: a) receiving input information for selecting a target object; b) transmitting and receiving ultrasound signals to and from the target object to thereby output ultrasound data; c) forming a 3D ultrasound image based on the ultrasound data; and d) performing a position arrangement of the 3D ultrasound image based on reference position information corresponding to the input information, wherein the reference position information is stored in a storage unit corresponding to a plurality of target objects.

The Summary is provided to introduce a selection of concepts in a simplified form that are further described below in the Detailed Description. This Summary is not intended to identify key or essential features of the claimed subject matter, nor is it intended to be used in determining the scope of the claimed subject matter.

DETAILED DESCRIPTION

A detailed description may be provided with reference to the accompanying drawings. One of ordinary skill in the art may realize that the following description is illustrative only and is not in any way limiting. Other embodiments of the present invention may readily suggest themselves to such skilled persons having the benefit of this disclosure.

Figure 1:
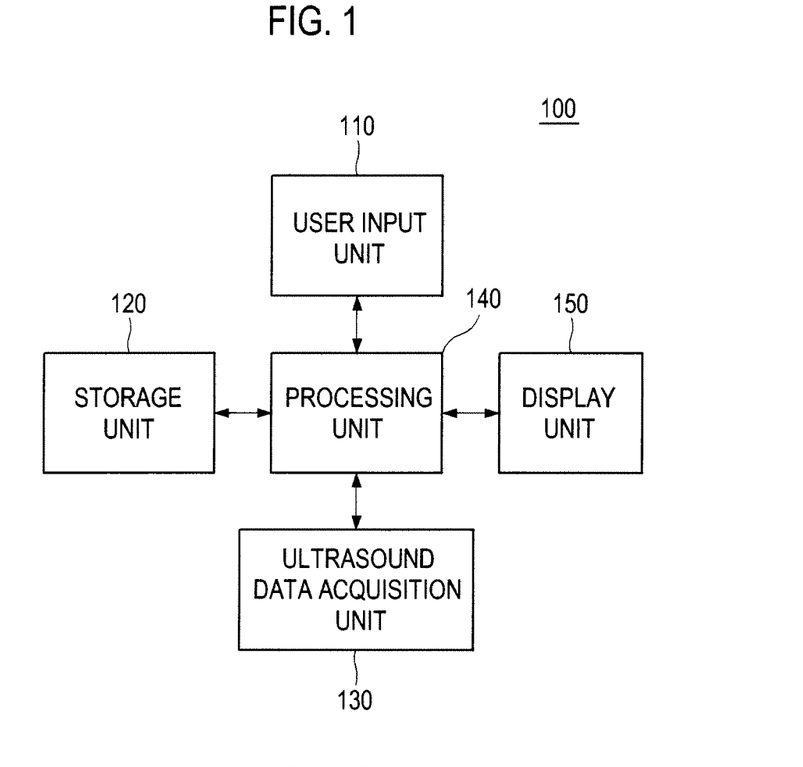
FIG. 1 is a block diagram showing an illustrative embodiment of an ultrasound system.

An ultrasound system 100 in accordance with an illustrative embodiment is shown in FIG. 1. As depicted therein, the ultrasound system 100 may include a user input unit 110. The user input unit 110 may receive input information from a user. The input information may be information for selecting a target object to form a 3D (three-dimensional) ultrasound image from a subject (e.g., a patient). The target object may include a heart, a liver, a blood vessel, a lesion or the like. However, the target object may not be limited thereto. The user input unit 110 may include a control panel, a mouse, a keyboard or the like, although it may not be limited thereto.

The ultrasound system 100 may further include a storage unit 120. The storage unit 120 may store a plurality of reference position information each corresponding to a plurality of target objects. The reference position information may be information for arranging the 3D ultrasound image to a predetermined position. In one embodiment, the reference position information may include a plurality of predetermined pixel distances between pixels corresponding to contour points of the target object. The storage unit 120 may store a mapping table providing the plurality of reference position information each corresponding to a plurality of target objects.

The ultrasound system 100 may further include an ultrasound data acquisition unit 130. The ultrasound data acquisition unit 130 may transmit and receive ultrasound signals to and from a target object to thereby output ultrasound data. The ultrasound data acquisition unit 130 may include a transmit (Tx) signal generating section 131, as shown in FIG. 2.

Figure 2:
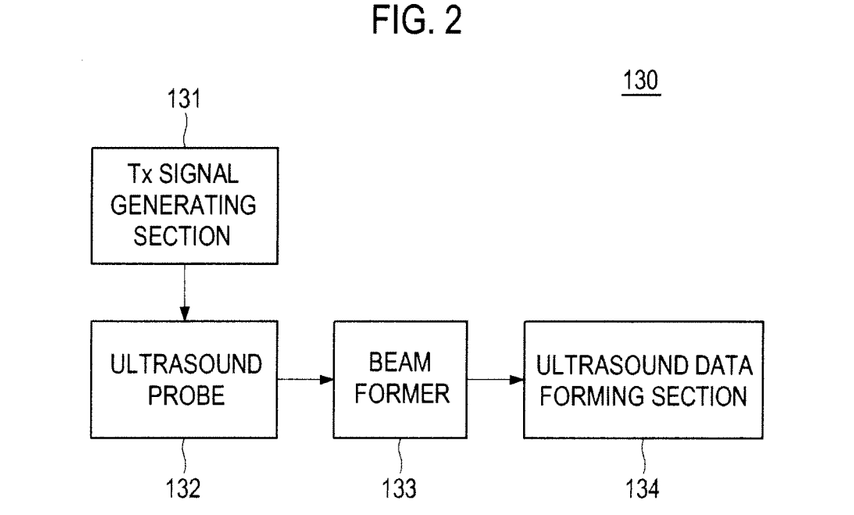
FIG. 2 is a block diagram showing an illustrative embodiment of an ultrasound data acquisition unit.
Figure 3:
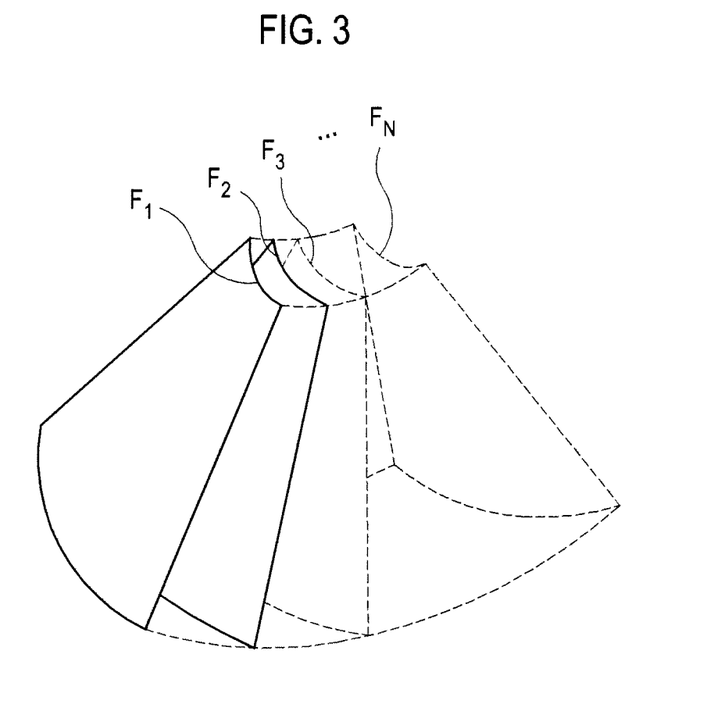
FIG. 3 is a schematic diagram showing an example of acquiring ultrasound data corresponding to a plurality of frames.

Referring to FIG. 2, the Tx signal generating section 131 may be configured to generate Tx signals. The Tx signal generating section 131 may perform the generation of the Tx signals at every predetermined time to thereby form a plurality of Tx signals for obtaining each of frames $F_i(1 \leq i \leq N)$ representing the target object, as shown in FIG. 3. The frames $F_i(1 \leq i \leq N)$ may represent a plurality of sectional planes of the target object.

The ultrasound data acquisition unit 130 may further include an ultrasound probe 132 containing a plurality of elements for reciprocally converting between ultrasound signals and electrical signals. The ultrasound probe 132 may be configured to transmit ultrasound signals into the target object in response to the Tx signals. The ultrasound probe 132 may further receive echo signals reflected from the target object to thereby output received signals. The received signals may be analog signals. The ultrasound probe 132 may include a three-dimensional mechanical probe, a two-dimensional array probe or the like.

The ultrasound data acquisition unit 130 may further include a beam former 133. The beam former 133 may convert the received signals into digital signals. The beam former 133 may further apply delays to the digital signals in consideration of distances between the plurality of elements of the ultrasound probe 132 and focal points to thereby output digital receive-focused signals.

The ultrasound data acquisition unit 130 may further include an ultrasound data forming section 134. The ultrasound data forming section 134 may form ultrasound data corresponding to each of the frames $F_i(1 \leq i \leq N)$ based on the digital receive-focused signals.

Figure 4:
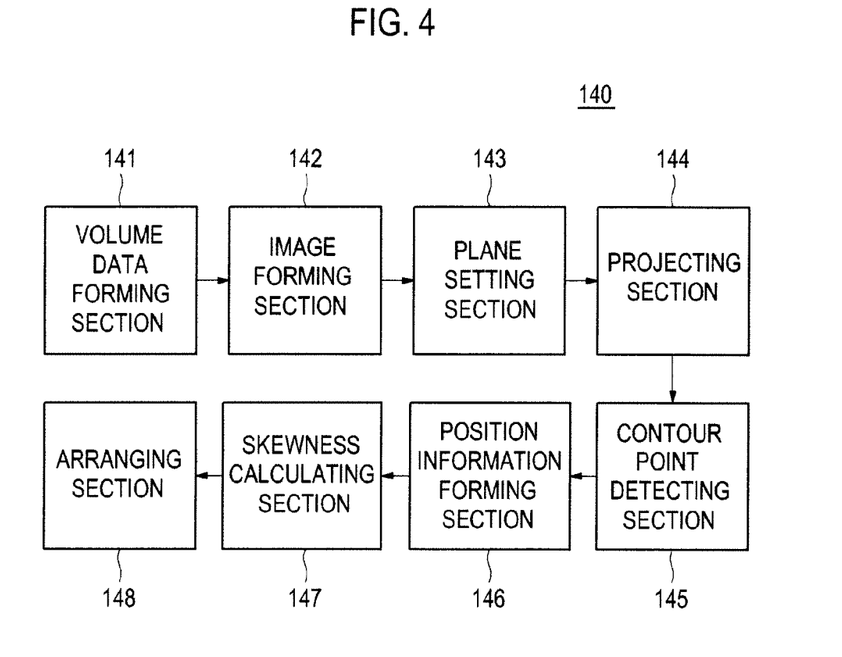
FIG. 4 is a block diagram showing an illustrative embodiment of a processing unit.

Referring back to FIG. 1, the ultrasound system 100 may further include a processing unit 140, which may be coupled to the user input unit 110, the storage unit 120 and the ultrasound data acquisition unit 130. FIG. 4 is a block diagram showing an illustrative embodiment of the processing unit 140. Referring to FIG. 4, the processing unit 140 may include a volume data forming section 141, an image forming section 142, a plane setting section 143, a projecting section 144, a contour point detecting section 145, a position information forming section 146, a skewness calculating section 147 and an arranging section 148.

The volume data forming section 141 may synthesize the ultrasound data corresponding to the frames $F_i(1 \leq i \leq N)$ to thereby form volume data including the frames $F_i(1 \leq i \leq N)$. The volume data may include a plurality of voxels having brightness values.

The image forming section 142 may render the volume data provided from the volume data forming section 141 to thereby form the 3D ultrasound image. The methods of rendering the volume data are well known in the art. Thus, they have not been described in detail so as not to unnecessarily obscure the present invention.

Figure 5:
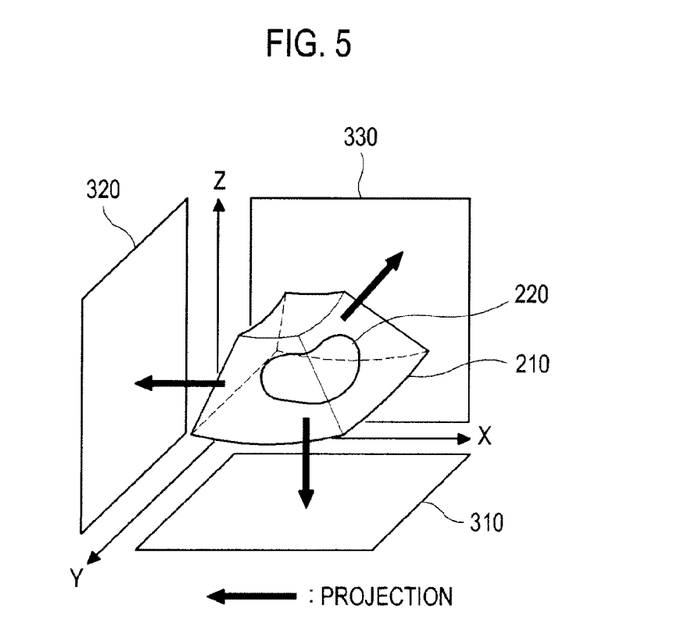
FIG. 5 is a schematic diagram showing an example of projecting a 3D ultrasound image to an XY plane, a YZ plane and an XZ plane.

The plane setting section 143 may set a plurality of planes for projecting the 3D ultrasound image. In one embodiment, the plane setting section 143 may set an XY plane 310, a YZ plane 320 and an XZ plane 330 for projecting the 3D ultrasound image 210, as shown in FIG. 5. In FIG. 5, reference numeral 220 represents the target object.

The projecting section 144 may project the 3D ultrasound image to the XY plane 310, the YZ plane 320 and the XZ plane 330 to thereby form 2D (two-dimensional) projection images on the XY plane 310, the YZ plane 320 and the XZ plane 330. The methods of projecting the 3D ultrasound image are well known in the art. Thus, they have not been described in detail so as not to unnecessarily obscure the present invention.

The contour point detecting section 145 may detect contour points of the target object in the 2D projection images of the XY plane 310, the YZ plane 320 and the XZ plane 330. The contour point may be detected by using an edge mask such as Sobel, Prewitt, Robert, Canny mask or the like. The contour point may be detected based on the differences between eigenvalues using structure tensors.

The position information forming section 146 may calculate pixel distances between pixels corresponding to the detected contour points to thereby form position information including the pixel distances.

Figure 6:
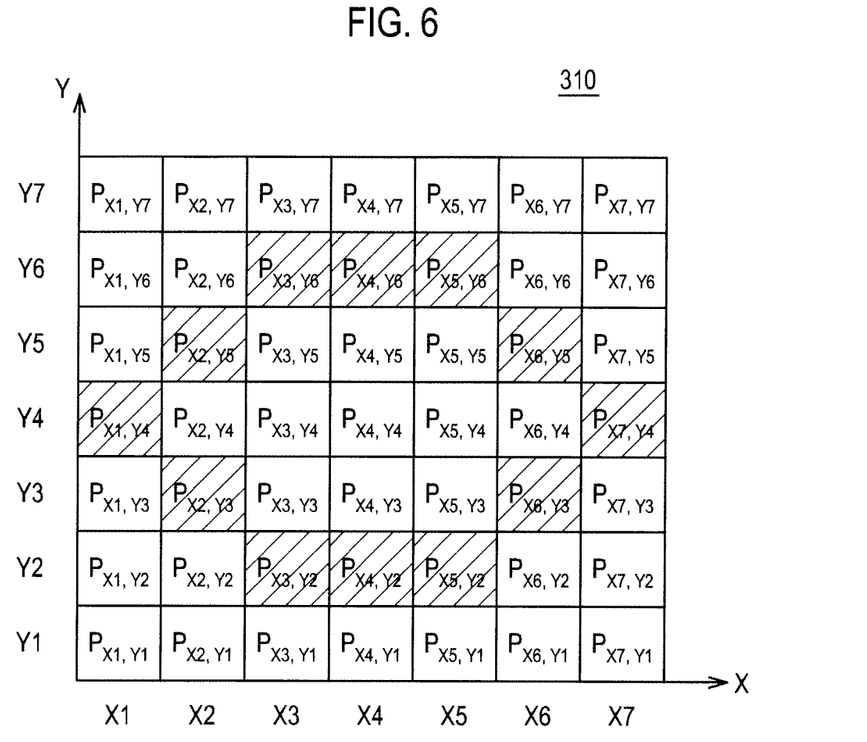
FIG. 6 is a schematic diagram showing an example of a 2D projection image of the XY plane.

In one embodiment, the position information forming section 146 may calculate pixel distances between the pixels $P_{X1,Y4}$, $P_{X2,Y3}$, $P_{X2,Y5}$, $P_{X3,Y2}$, $P_{X3,Y6}$, $P_{X4,Y2}$, $P_{X4,Y6}$, $P_{X5,Y2}$, $P_{X5,Y6}$, $P_{X6,Y3}$, $P_{X6,Y5}$ and $P_{X7,Y4}$ corresponding to the detected contour points in the 2D projection image of the XY plane 310, as shown in FIG. 6. More particularly, the position information forming section 146 may calculate pixel distance $(D_{X2}=2)$ between pixels $P_{X2,Y3}$ and $P_{X2,Y5}$ located in X2, pixel distance $(D_{X3}=4)$ between pixels $P_{X3,Y2}$ and $P_{X3,Y6}$ located in X3, pixel distance $(D_{X4}=4)$ between pixels $P_{X4,Y2}$ and $P_{X4,Y6}$ located in X4, pixel distance $(D_{X5}=4)$ between pixels $P_{X5,Y2}$ and $P_{X5,Y6}$ located in X5, and pixel distance $(D_{X6}=2)$ between pixels $P_{X6,Y3}$ and $P_{X6,Y5}$ located in X6. Also, the position information forming section 146 may further calculate pixel distance $(D_{Y21}=1)$ between pixels $P_{X3,Y7}$ and $P_{X4,Y2}$ located in Y2, pixel distance $(D_{Y22}=1)$ between pixels $P_{X4,Y2}$ and $P_{X5,Y2}$ located in Y2, pixel distance $(D_{Y23}=2)$ between pixels $P_{X3,Y2}$ and $P_{X5,Y2}$ located in Y2, pixel distance $(D_{Y3}=4)$ between pixels $P_{X2,Y3}$ and $P_{X6,Y3}$ located in Y3, pixel distance $(D_{Y4}=6)$ between pixels $P_{X1,Y4}$ and $P_{X7,Y4}$ located in Y4, pixel distance $(D_{Y5}=4)$ between pixels $P_{X2,Y5}$ and $P_{X6,Y5}$ located in Y5, pixel distance $(D_{Y61}=1)$ between pixels $P_{X3,Y6}$ and $P_{X4,Y6}$ located in Y6, pixel distance $(D_{Y62}=1)$ between pixels $P_{X4,Y6}$ and $P_{X5,Y6}$ located in Y6, and pixel distance $(D_{Y63}=2)$ between pixels $P_{X3,Y6}$ and $P_{X5,Y6}$ located in Y6.

Figure 7:
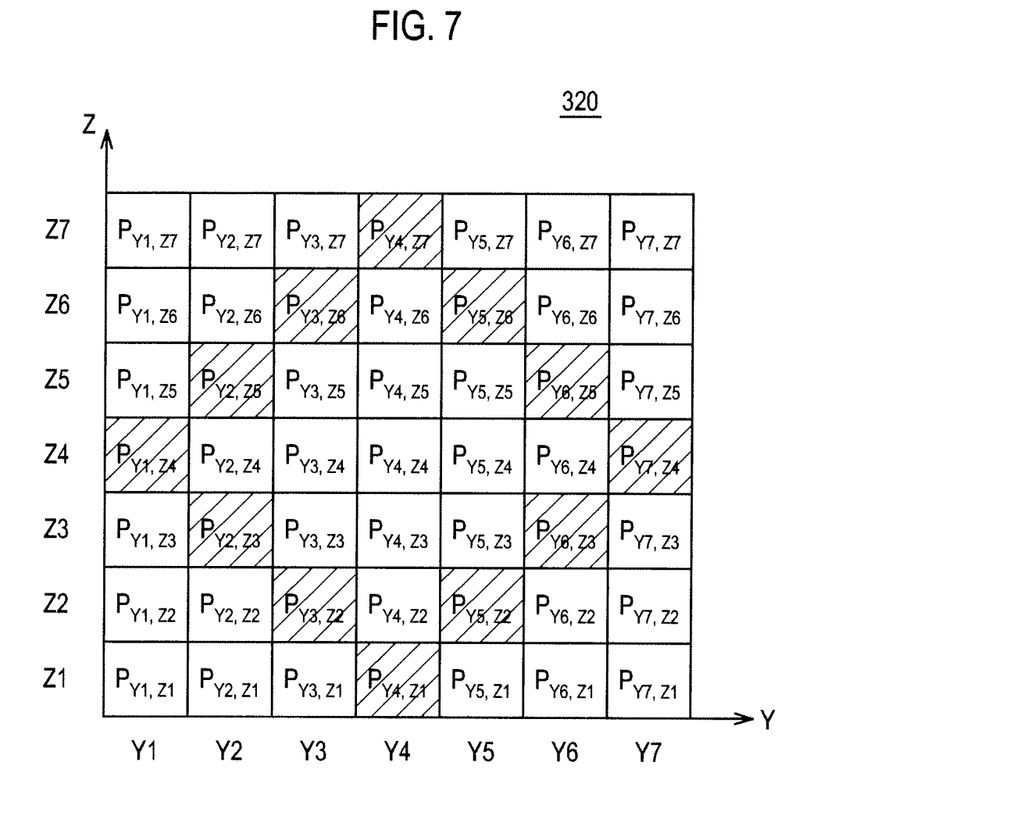
FIG. 7 is a schematic diagram showing an example of a 2D projection image of the YZ plane.
Figure 8:
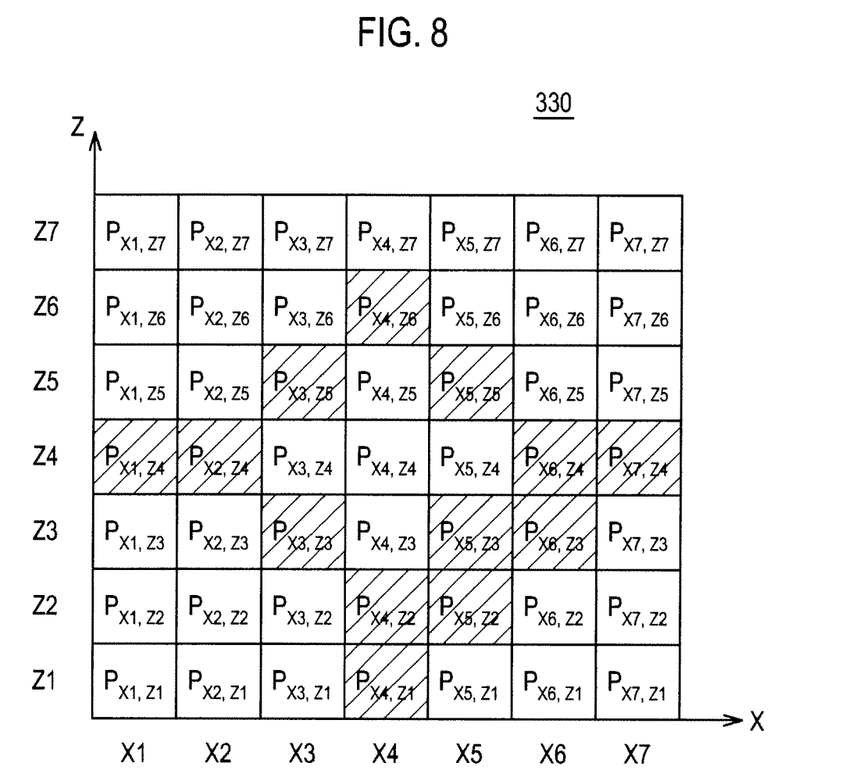
FIG. 8 is a schematic diagram showing an example of a 2D projection image of the XZ plane.

Similarly, the position information forming section 146 may further calculate pixel distances between the pixels $P_{Y1,Z4}$, $P_{Y2,Z3}$, $P_{Y2,Z5}$, $P_{Y3,Z2}$, $P_{Y3,Z6}$, $P_{Y4,Z1}$, $P_{Y4,Z7}$, $P_{Y5,Z2}$, $P_{Y5,Z6}$, $P_{Y6,Z3}$, $P_{Y6,Z5}$ and $P_{Y7,Z4}$ corresponding to the detected contour points in the 2D projection image of the YZ plane 320, as shown in FIG. 7. Also, the position information forming section 146 may further calculate pixel distances between the pixels $P_{X1,Z4}$, $P_{X2,Z4}$, $P_{X3,Z3}$, $P_{X3,Z5}$, $P_{X4,Z1}$, $P_{X4,Z2}$, $P_{X4,Z6}$, $P_{X5,Z2}$, $P_{X5,Z3}$, $P_{X5,Z5}$, $P_{X6,Z3}$, $P_{X6,Z4}$ and $P_{X7,Z4}$ corresponding to the detected contour points in the 2D projection image of the XZ plane 330, as shown in FIG. 8. The position information forming section 146 may form the position information including the calculated pixel distances.

The skewness calculating section 147 may retrieve reference position information corresponding to the input information from the storage unit 120. The skewness calculating section 147 may further calculate skewness based on the position information and the retrieved reference position information to thereby form skewness information. In one embodiment, the skewness calculating section 147 may calculate skewness between the pixel distances of the position information and the predetermined pixel distances of the retrieved reference position information to thereby form the skewness information. However, the methods of calculating the skewness may not be limited thereto.

The arranging section 148 may perform a position arrangement of the 3D ultrasound image based on the skewness information provided from the skewness calculating section 147. In one embodiment, the arranging section 148 may compare the skewness of the skewness information with a predetermined threshold value. If the skewness is larger than the threshold value, then the arranging section 148 may calculate difference between the skewness and the threshold value. The arranging section 148 may further perform the position arrangement of the 3D ultrasound image by moving or rotating the 3D ultrasound image based on the calculated difference.

The projecting section 144, the contour point detecting section 145, the position information forming section 146, the skewness calculating section 147 and the arranging section 148 of the processing unit 140 may perform the position arrangement of the 3D ultrasound image until the skewness is smaller than the threshold value. That is, the 3D ultrasound image is arranged to the predetermined position.

Referring back to FIG. 1, the ultrasound system 100 may further include a display unit 150. The display unit 150 may display the 3D ultrasound image.

In another embodiment, the present invention may provide a computer readable medium comprising computer executable instructions configured to perform following acts: a) receiving input information for selecting a target object; b) transmitting and receiving ultrasound signals to and from the target object to thereby output ultrasound data; c) forming a 3D ultrasound image based on the ultrasound data; and d) performing a position arrangement of the 3D ultrasound image based on reference position information corresponding to the input information, wherein the reference position information is stored in a storage unit corresponding to a plurality of target objects. The computer readable medium may comprise a floppy disk, a hard disk, a memory, a compact disk, a digital video disk, etc.

Although embodiments have been described with reference to a number of illustrative embodiments thereof, it should be understood that numerous other modifications and embodiments can be devised by those skilled in the art that will fall within the spirit and scope of the principles of this disclosure. More particularly, numerous variations and modifications are possible in the component parts and/or arrangements of the subject combination arrangement within the scope of the disclosure, the drawings and the appended claims. In addition to variations and modifications in the component parts and/or arrangements, alternative uses will also be apparent to those skilled in the art.

What is claimed is:

1. An ultrasound system, comprising:
a user input which receives input information for selecting a target object from a plurality of target objects;
an ultrasound probe which transmits and receives ultrasound signals to and from the target object to thereby output ultrasound data; and
a processor connected to and in communication with the user input and the ultrasound probe, the processor forms a three-dimensional (3D) ultrasound image according to the ultrasound data, retrieves reference position information corresponding to the selected target object, compares position information corresponding to the 3D ultrasound image with the retrieved reference position information to form a comparison, and performs a position arrangement of the 3D ultrasound image according to the comparison.

2. The ultrasound system of claim 1, wherein the processor synthesizes the ultrasound data to form volume data;
renders the volume data to form the 3D ultrasound image;
sets a plurality of planes for projecting the 3D ultrasound image;
projects the 3D ultrasound image to the plurality of planes to form two-dimensional (2D) projection images;
detects contour points of the target object in the 2D projection images;
compares pixel distances between pixels corresponding to the detected contour points with the predetermined pixel distances of reference position information corresponding to the input information to calculate skewness;
calculates the pixel distances between pixels corresponding to the detected contour points to thereby form the position information including the calculated pixel distances;
calculates the skewness according to the comparison; and
calculates a difference between the calculated skewness and a predetermined threshold value and moves or rotates the 3D ultrasound image by the calculated difference to perform the position arrangement of the 3D ultrasound image.

3. The ultrasound system of claim 2, wherein the planes comprise an XY plane, a YZ plane and an XZ plane.

4. The ultrasound system of claim 3, wherein the processor calculates a plurality of first pixel distances between pixels corresponding to the detected contour points in the 2D projection image of the XY plane, calculates a plurality of second pixel distances between pixels corresponding to the detected contour points in the 2D projection image of the YZ plane, calculates a plurality of third pixel distances between pixels corresponding to the detected contour points in the 2D projection image of the XZ plane and forms the position information including the plurality of first, second and third pixel distances.

5. The ultrasound system of claim 4, wherein the reference position information comprises a plurality of predetermined pixel distances between pixels corresponding to contour points of the target object.

6. The ultrasound system of claim 5, wherein the processor calculates the skewness between the plurality of first, second and third pixel distances of the position information and the plurality of predetermined pixel distances of the reference position information.

7. The ultrasound system of claim 6, wherein the processor calculates the difference between the skewness and the threshold value when the skewness is larger than the threshold value.

8. The ultrasound system of claim 1, wherein the processor forms the position information, calculates skewness according to the position information and retrieved reference position information, and performs the position arrangement of the 3D ultrasound image according to the skewness.

9. A method of arranging a three-dimensional (3D) ultrasound image, comprising:

a) receiving input information for selecting a target object from a plurality of target objects;
b) transmitting and receiving ultrasound signals to and from the target object to thereby output ultrasound data;
c) forming a 3D ultrasound image according to the ultrasound data;
d) retrieving reference position information corresponding to the selected target object;
e) comparing position information corresponding to the 3D ultrasound image with the retrieved reference position information to form a comparison; and
f) performing a position arrangement of the 3D ultrasound image according to the comparison.

10. The method of claim 9, further comprising:
synthesizing the ultrasound data to form volume data;
rendering the volume data to form the 3D ultrasound image;
setting a plurality of planes for projecting the 3D ultrasound image;
projecting the 3D ultrasound image to the plurality of planes to form two-dimensional (2D) projection images;
detecting contour points of the target object in the 2D projection images;
comparing pixel distances between pixels corresponding to the detected contour points with the predetermined pixel distances of reference position information corresponding to the input information to calculate skewness;
calculating the pixel distances between pixels corresponding to the detected contour points to thereby form the position information including the calculated pixel distances;
calculating the skewness according to the comparison;
calculating a difference between the calculated skewness and a predetermined threshold value; and
moving or rotating the 3D ultrasound image by the calculated difference to perform the position arrangement of the 3D ultrasound image.

11. The method of claim 10, wherein the planes comprise an XY plane, a YZ plane and an XZ plane.

12. The method of claim 11, the calculating the pixel distances comprises:
calculating a plurality of first pixel distances between pixels corresponding to the contour points in the 2D projection image of the XY plane;
calculating a plurality of second pixel distances between pixels corresponding to the contour points in the 2D projection image of the YZ plane;
calculating a plurality of third pixel distances between pixels corresponding to the contour points in the 2D projection image of the XZ plane; and
forming the position information including the plurality of first, second and third pixel distances.

13. The method of claim 12, wherein the reference position information comprises a plurality of predetermined pixel distances between pixels corresponding to contour points of the target object.

14. The method of claim 13, wherein the calculating the skewness comprises:
calculating skewness between the plurality of first, second and third pixel distances of the position information and the plurality of predetermined pixel distances of the reference position information.

15. The method of claim 14, wherein the moving or rotating the 3D ultrasound image comprises:
calculating difference between the skewness and the threshold value when the skewness is larger than the threshold value.

16. The method of claim 9, further comprising:
forming the position information; and
calculating skewness according to the position information and retrieved reference position information,
wherein the performing the position arrangement of the 3D ultrasound image comprises moving or rotating the 3D ultrasound image according to the skewness.

17. A non-transitory computer readable medium comprising computer executable instructions configured to perform the following acts:
a) receiving input information for selecting a target object from a plurality of target objects;
b) transmitting and receiving ultrasound signals to and from the target object to thereby output ultrasound data;
c) forming a three-dimensional (3D) ultrasound image according to the ultrasound data;
d) retrieving reference position information corresponding to the selected target object;
e) comparing position information corresponding to the 3D ultrasound image with the retrieved reference position information to form a comparison; and
f) performing a position arrangement of the 3D ultrasound image according to the comparison.

* * * * *